United States Patent [19]

Claeson et al.

[11] 4,335,204
[45] Jun. 15, 1982

[54] EASILY SPLIT SUBSTRATES FOR THE QUANTIFICATION OF PROTEASES

[75] Inventors: Karl G. Claeson, Lidingö; Leif E. Aurell, Särö; Leif R. Simonsson, Hising Backa; Salo Arielly, Kungsbacka, all of Sweden

[73] Assignee: Kabi AB, Stockholm, Sweden

[21] Appl. No.: 247,488

[22] Filed: Mar. 25, 1981

Related U.S. Application Data

[62] Division of Ser. No. 7,447, Jan. 29, 1979, Pat. No. 4,279,810.

[30] Foreign Application Priority Data

Feb. 7, 1978 [SE] Sweden .............................. 7801373

[51] Int. Cl.$^3$ .............................................. C12Q 1/38
[52] U.S. Cl. ........................................ 435/23; 435/13
[58] Field of Search .............................. 435/24, 13, 23

[56] References Cited

U.S. PATENT DOCUMENTS

| | | | |
|---|---|---|---|
| 3,884,896 | 5/1975 | Blomback et al. | 435/13 X |
| 3,886,136 | 5/1975 | Claeson et al. | 435/13 X |
| 4,016,042 | 4/1977 | Svendsen | 435/23 |
| 4,028,318 | 6/1977 | Aurell et al. | 435/23 |
| 4,070,245 | 1/1978 | Svendsen | 435/23 X |
| 4,276,375 | 6/1981 | Claeson et al. | 435/23X |

*Primary Examiner*—Esther M. Kepplinger
*Attorney, Agent, or Firm*—Pollock, Vande Sande & Priddy

[57] ABSTRACT

Easily split enzyme substrates for the quantification of proteases having the general formula

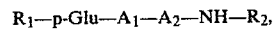

$$R_1-p\text{-}Glu-A_1-A_2-NH-R_2,$$

where
$R_1$ = H or a protective group, preferably t-butyloxycarbonyl, benzyloxycarbonyl;
$A_1$ = Gly, Ala, Val, Leu, Ile, Ser, Thr, Pro, Pip, Phe or Tyr;
$A_2$ = Arg or Lys;
$R_2$ = an aromatic, possibly substituted, hydrocarbon group, wherein —NH—$R_2$ is a physico-chemically determinable group, preferably a chromogenic or fluorogenic group which is split by a present enzyme and then forms a cleavage product of the formula $H_2N-R_2$ the amount of which can be quantified.

Processes for the production of said substrates. Method in the laboratory diagnostics of proteases using said substrates.

3 Claims, No Drawings

EASILY SPLIT SUBSTRATES FOR THE QUANTIFICATION OF PROTEASES

This is a division, of application Ser. No. 7,447, filed Jan. 29, 1979 U.S. Pat. No. 4,279,810.

TECHNICAL FIELD

This invention relates to novel easily split substrates intended to be used as reagents in the quantitative determination of serine proteases and SH-proteases, or in the study of reactions where serine proteases are formed, inhibited or consumed, or in the determination of factors influencing, or participating in such reactions.

BACKGROUND ART

Lately, a number of synthetic peptide substrates have been described. The majority of these present a tripeptide chain where either the amino group of the N-terminal amino acid is blocked by an acyl group or is free but then having the D-configuration. The C-terminal amino acid is blocked by a chromogenic or a fluorogenic group which is split off in the reaction of the enzyme with the substrate. The thus formed, liberated chromophoric or fluorescent group can be quantitatively determined by photometric or fluorescence-photometric methods. The enzymatic activity can be calculated by measuring the amount of cleavage product liberated per time unit.

DISCLOSURE OF INVENTION

The short peptide chain is of importance to the affinity of the substrate to the enzyme. In this connection it seems to be essential that the N-terminal amino acid either has the L-form with an acylated amino group, or the D-form with a free amino group. We have now established that substrates with an N-terminal pyroglutamic acid are very easily split by a number of serine proteases. Pyroglutamic acid with its α-amino group not being free but acylated by ring closure, that is lactam of glutamic acid, has not been used before in peptides intended for use as substrates in the determination of enzymes. The novel chromogenic substrates, according to the invention, are represented by the following general formula:

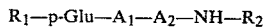

$$R_1\text{—p-Glu—}A_1\text{—}A_2\text{—NH—}R_2$$

or salts thereof wherein
  $R_1$ may be hydrogen or a protective group, preferably t-butyloxycarbonyl or benzyloxycarbonyl,
  $A_1$ may be chosen from the amino acids Gly, Ala, Val, Leu, Ile, Ser, Thr, Pro, Pip, Phe or Tyr,
  $A_2$ may be Arg or Lys,
  $R_2$ may be an aromatic, possibly substituted, hydrocarbon group wherein —NH—$R_2$ constitutes a physico-chemically determinable group, preferably a chromogenic or fluorogenic group split by the mentioned enzyme and then forming a cleavage product of the formula $H_2N$—$R_2$ the amount of which can be quantified.

In the synthesis of the novel substrates according to the invention, conventional protective groups and coupling methods well known in peptide chemistry are used.

The principle of the synthesis may be a step-wise coupling of the amino acids to the C-terminal arginyl or lysyl rest, either initially provided with a linked-on determinable group (—$HN_2$—$R_2$ according to the formula) which then serves as a carboxylic protective group, or provided with a carboxylic protective group which is removable and, in that case, the determinable group is linked to the protected tripeptide derivative, or again the N-terminal protected dipeptide fraction may be synthetized separately and then linked to the arginyl or lysyl rest, with or without determinable group, according to the foregoing.

Whichever of these synthesis routes is chosen, the intermediary and end products are purified by recrystallization and/or gel filtration chromatography.

The invention is illustrated by the following examples.

In the thin-layer chromatography analysis of the eluates and the product, glass plates with silica gel $F_{254}$ (Merck) are used as an absorption medium. The solvent systems used are:
  A: n-butanol:HOAc:water, 3:2:1 (volume)
  $P_1$: chloroform:MeOH, 9:1 (volume)

After thin-layer chromatography, the plates are first studied in UV light (254 nm) and then sprayed with ninhydrine and subsequently treated with dicarboxidine/chlorine. The stated $R_f$-values are the results of single chromatographs.

The abbreviations used below are as follows:
  The abbreviations refer to amino acid rests. The free amino acid or peptide is indicated by an H- at the amino group and an -OH at the carboxyl group. The amino group is always indicated to the left and the carboxyl group to the right.

Unless otherwise stated, all amino acids, with the exception of Gly, have the L-configuration.
  Ala = Alanine
  Arg = Arginine
  Gly = Glycine
  Ile = Isoleucine
  Leu = Leucine
  Lys = Lysine
  p-Glu = pyroglutamic acid
  Phe = Phenylalanine
  Pip = Pipecolic acid
  Pro = Proline
  Ser = Serine
  Thr = Threonine
  Tyr = Tyrosine
  Val = Valine
  Further abbreviations:
  HOAc = Acetic acid
  Bz = Benzoyl
  Cbo = Carbobenzoxy
  DCCI = Dicyclohexylcarbodiimide
  $PCl_3$ = Phosphorous trichloride
  DMF = Dimethylformamide
  $Et_3N$ = Triethylamine
  HOBT = Hydroxybenzotriazol
  DCHA = Dicyclohexylamine
  DCU = Dicyclohexylurea
  EtOH = Ethanol
  MeOH = Methanol
  EtOAc = Ethyl acetate
  OpNP = p-Nitrophenoxy
  pNA = p-Nitroanilide
  TFA = Trifluoroacetic acid
  β-NA = β-Naphthylamide
  4-MeO-β-NA = 4-Methoxyβ-naphtylamide
  7-A-4-M-C = 7-Amino-4-methyl-coumarin

EXAMPLE I p-Glu-Gly-Arg-pNA.HCl, (m.w.=498.9)

Ia Cbo-Gly-Arg($NO_2$)pNA, (m.v.=530.5)

175 ml of concentrated HOAc and 105 ml of 5.6 M HBr in HOAc are added to 35 g (0.074 mol) of Cbo-Arg($NO_2$)-pNA. The mixture is allowed to react and stirred for 30 minutes after the reaction solution has cleared. The mixture is then poured into approximately 2 l of dry ether while being stirred vigorously. The resulting precipitate is filtered and washed with dry ether and then vacuum dried over NaOH. The obtained HBr salt of H-Arg($NO_2$)-pNA is dissolved in 150 ml of dry, distilled DMF and neutralized at a low temperature ($-10°$ C.) with $Et_3N$ until a slightly basic reaction is obtained on a moistened pH-paper over the reaction mixture. (Usually approximately 1.5 equivalents of HBr are neutralized.) The resulting $Et_3$NHBr is filtered off. Under cool conditions, 1.1 equivalent=0.81 mol=26.8 g of Cbo-Gly-OpNP is added to the reaction mixture; after 30 minutes another ½ equivalent=5.2 ml of $Et_3N$ is added. The mixture is allowed to react over night at room temperature and thereafter evaporated in vacuo to give an oil. The oil is triturated in an aqueous solution of 2 percent of $NaHCO_3$ and then dissolved in hot MeOH and crystallized while it is stirred and cooled. The resulting crystals are filtered off and washed with cold MeOH. TLC shows only minor impurifications and the product is, therefore, recrystallized in the same solvent. This results in white crystals, pure according to TLC.

Yield: 34 g (86%) of Ia.

$R_f=0.20$ ($P_1$)

$[\alpha]_D^{23} -35.4°$ (c 0.3 MeOH)

Ib' Cbo-p-Glu-OH, (m.w.=263.3)

56.3 g (0.20 mol) of Cbo-Glu-OH is dissolved in 400 ml of EtOAc, and 49.4 g (0.24 mol) of DCCI dissolved in 60 ml of EtOAc is added and stirred in an ice bath. After two hours, the resulting DCU is filtered and the remaining solution evaporated to dryness. The product (anhydride of Cbo-Glu) is crystallized from EtOAc and petroleum ether. The anhydride is dissolved in 120 ml of dioxane plus 260 ml ether, and then 48 ml of DCHA dissolved in ether to a volume of 100 ml is added. After a while, Cbo-p-Glu.DCHA precipitates. It is stirred for approximately 1 hour and then the formed DCHA salt is filtered off and washed with ether and EtOAc. The DCHA salt is suspended in EtOAc and shaken with 25 g (0.18 mol) of $KHSO_4$ dissolved in water, and the Cbo-p-Glu-OH thus formed then goes into the EtOAc-phase. The EtOAc-phase is washed with 10% NaCl in $H_2O$ and dried over $Na_2SO_4$ (there is a risk of the product precipitating). The EtOAc-phase is evaporated to a small volume and precipitated with petroleum ether; this results in heavy crystals of Ib' which are pure according to TLC.

Yield: 36.9 g (80%) of Ib'.

$R_f=0.45$ (A)

$[\alpha]_D^{24} -30.3°$ (c 1.0 MeOH)

Ib Cbo-p-Glu-Gly-Arg($NO_2$)pNA, (m.w.=641.6), 10.25 g (18.3 mmol) of H-Gly-Arg($NH_2$)pNa HBr, obtained by deprotecting Cbo-Gly-Arg($NO_2$)pNA with HBr according to the procedure as described in Ia, is dissolved in 35 ml of dry DMF and neutralized at a low temperature ($-10°$ C.) with $Et_3N$ until a basic reaction is obtained on moistened pH-paper. The resulting EtNHBr is filtered off. 2.47 g (18.3 mmol) of HOBT and 5.26 g (20 mmol) of Cbo-p-Glu-OH (Ib') are added to the reaction mixture and, thereafter, 4.53 g (22 mmol) of DCCI dissolved in a small amount of DCCI is added at a low temperature. The mixture is allowed to react over night at room temperature; subsequently, the reaction solution is evaporated to an oil. The oil is triturated with 2 percent $NaHCO_3$ in water, and with pure water. The obtained solid compound is dissolved in a small amount of acetone, and then hot MeOH and a small amount of water are added. The product is crystallized while it is cooled and stirred, and the resulting crystals are filtered off. The Ib obtained is pure according to TLC. After careful vacuum drying, 8.90 g (76%) of Ib is obtained.

$R_f=0.06$ ($P_1$)

$[\alpha]_D^{21} -21.5°$ (c 0.8 DMF)

I. 0.8 g (1.25 mmol) of Ib is deprotected with 30 ml of HF at 0° C. for 1 hour in the presence of 0.6 ml of anisole. After evaporation in vacuo, the product is dissolved in approximately 30 ml of 2 percent HOAc and washed with a small amount of ether. The $H_2O$-phase is chromatographed on a column with Sephadex G-15 (Pharmacia Fine Chemicals) in 2 percent of HOAc with the same medium for eluation. The fraction with the pure acetate of I is lyophilized and ion-exchanged on a column with QAE-25 (Pharmacia Fine Chemicals) in chloride form with EtOH—$H_2O$ (1:1) with the same medium for eluation.

The fraction with the pure hydrochloride of I is lyophilized.

Yield: 485 mg (78%) of I.

TLC [$R_f=0.29$ (A)] only shows one spot $[\alpha]_D^{24} -54.1°$ (c 1.0, 50% HOAc/$H_2O$)

Examples II–XIII as described in Table I are effected in the same way, in principle, as the foregoing examples; only the physical data, yields, as well as coupling and purification methods are therefore listed in this table form.

EXAMPLE XIV p-Glu-Gly-Arg-4-MeO-β-NA.HCl, (m.w.=534.0),

XIVa p-Glu-Gly-Arg-OH.HCl, (m.w.=378.8).

Trypsin (Novo, 400 μl of a solution of 2.0 mg trypsin per ml of 1 mM of HCl) is added to a solution of 250 mg (0.50 mmol) of p-Glu-Gly-Arg-pNA.HCl (S-2444) in 100 ml of 0.1 M $NaHCO_3$ in $H_2O$. The release of pNA is followed in a spectrophotometer at 405 nm. The release is finished after approximately 45 minutes and the solution is thereafter acidified with HOAc to a pH of ~4. It is then evaporated to dryness, dissolved in MeOH and chromatographed on a column with LH-20 (Pharmacia Fine Chemicals) in MeOH with the same medium for eluation. The fraction with the pure acid XIVa is evaporated, dissolved in $H_2O$ and lyophilized.

Yield: 167 mg (88%) of XIVa which is pure according to TLC.

$R_f=0.08$ (A).

XIV:

A solution of 27 μl (0.25 mmol) of $PCl_3$ in 450 μl of dry pyridine is added, under moisture free conditions and in a ice-bath, to a solution of 105 mg (0.50 mmol) of 4-MeO-β-NA.HCl in 2.25 ml of dry pyridine. After being left for approximately 45 minutes at room temperature, all of the XIVa produced according to the foregoing is added. When the reaction ceases (after approximately 1 hour), the reaction mixture is evaporated to a dark-red oil (reduced pressure). The oil is dissolved in a small amount of EtOH-$H_2O$ (1:1) and applied to a column with QAE-25 (Pharmacia Fine Chemicals) in chloride form in EtOH—$H_2O$ (1:1) with the same medium for eluation. The fraction with the nearly pure hydrochloride of XIV is evaporated, dissolved again in a small amount of EtOH—H$_2$O (1:1), and the procedure is repeated. The thus obtained hydrochloride of XIV is pure and it is lyophilized after all alcohol has been evaporated.

Yield: 85 mg (36%) of XIV.
TLC (R$_f$=0.24 mg (A) shows only one spot.
[α]$_D^{22}$ −45.7° (c 0.6, 50% HOAc/H$_2$O)

EXAMPLE XV:

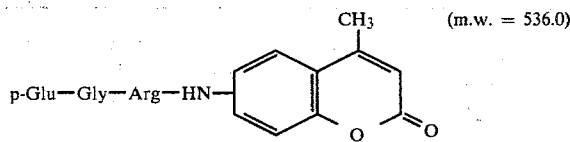

Procedure analogous to Example XIV, but with 88 mg (0.50 mmol) of 7-A-4-M-C as an amine instead of 4-MeO-β-NA.HCl.

Yield: 84 mg (32%) of XV.
TLC [R$_f$=0.25 (A)] shows only one spot.
[α]$_D^{25}$ −51.5° (c 1, 50% HOAc/H$_2$O).

TABLE I

| Substance | No. | R$_f$(System) | [α] | Solvent | Yield % |
|---|---|---|---|---|---|
| <Glu—Gly—Arg—pNA | I | 0.29 A | −54.1 | 50% HOAc | 78 |
| Cbo— NO$_2$ | Ia | 0.20 P$_1$ | −35.4 | MeOH | 86 |
| Cbo— NO$_2$ | Ib | 0.06 P | −21.5 | DMF | 76 |
| <Glu—Ser—Arg—pNA | II | 0.29 A | −58.2 | 50% HOAc | 81 |
| Boc— OBzl NO$_2$ | IIa | 0.19 P$_1$ | −24.9 | 95% EtOH | 84 |
| Cbo— OBzl NO$_2$ | IIb | 0.15 P$_1$ | −18.5 | DMF | 53 |
| <Glu—Thr—Arg—pNA | III | 0.32 A | −55.7 | 50% HOAc | 72 |
| Boc— OBzl NO$_2$ | IIIa | 0.18 P$_1$ | −25.4 | 95% EtOH | 85 |
| Cbo— OBzl NO$_2$ | IIIb | 0.16 P$_1$ | −25.2 | DMF | 65 |
| <Glu—Val—Arg—pNA | IV | 0.33 A | −66.5 | 50% HOAc | 56 |
| Cbo— NO$_2$ | IVa | 0.38 P$_1$ | + 5.4 | DMF | 86 |
| Cbo— NO$_2$ | IVb | 0.08 P$_1$ | −21.5 | DMF | 38 |
| <Glu—Ala—Arg—pNA | V | 0.25 A | −0.68 | 50% HOAc | 58 |
| Cbo— NO$_2$ | Va | 0.25 P$_1$ | + 2.4 | DMF | 85 |
| Cbo— NO$_2$ | Vb | 0.05 P$_1$ | −30.9 | DMF | 48 |
| <Glu—Pro—Arg—pNA | VI | 0.38 A | −95.6 | MeOH | 73 |
| Cbo— NO$_2$ | VIa | 0.45 P$_1$ | −33.0 | DMF | 82 |
| Cbo— NO$_2$ | VIb | 0.69 A | −66.3 | DMF | 63 |
| <Glu—Phe—Arg—pNA | VII | 0.36 A | −22.8 | 50% HOAc | 66 |
| Cbo— NO$_2$ | VIIa | 0.29 P$_1$ | + 5.5 | DMF | 94 |
| Cbo— NO$_2$ | VIIb | 0.03 P$_1$ | − 7.4 | DMF | 55 |
| D <Glu—Gly—Arg—pNA | VIII | 0.27 A | −41.8 | 50% HOAc | 53 |
| Cbo— NO$_2$ | VIIIa | 0.20 P$_1$ | −35.4 | MeOH | 86 |
| Cbo—D— NO$_2$ | VIIIb | 0.06 P$_1$ | − 5.7 | DMF | 72 |
| D <Glu—Pro—Arg—pNA | IX | 0.35 A | −99.0 | 50% HOAc | 56 |
| Cbo— NO$_2$ | IXa | 0.45 P$_1$ | −33.0 | DMF | 82 |
| Cbo—D— NO$_2$ | IXb | 0.10 P$_1$ | −37.7 | DMF | 66 |
| <Glu—Phe—Lys—pNA | X | 0.33 A | −28.7 | 50% HOAc | 69 |
| Boc— ε-Cbo | Xa | 0.55 P$_1$ | + 3.4 | DMF | 77 |
| Cbo— ε-Cbo | Xb | 0.40 P$_1$ | − 8.8 | DMF | 76 |
| <Glu—Leu—Lys—pNA | XI | 0.31 A | −61.7 | 50% HOAc | 85 |
| Boc— ε-Cbo | XIa | 0.49 P$_1$ | − 4.5 | DMF | 85 |
| Cbo— ε-Cbo | XIb | 0.48 P$_1$ | −27.2 | DMF | 57 |
| Cbo—pyro—Glu—Gly—Arg—pNA | XII | 0.32 A | −45.7 | 50% HOAc | 52 |
| H — | XIIa | 0.22 A | — | — | ~100 |

TABLE I-continued

| Substance | No. | $R_f$(System) | [α] | Solvent | Yield % |
|---|---|---|---|---|---|
| <Glu—Pro—Arg—β—NA | XIII | 0.24 A | −106 | MeOH | 57 |
| Cbo—$\overline{NO_2}$ | XIIIa | 0.52 P₁ | −44.9 | DMF | 82 |
| Cbo—$\overline{NO_2}$ | XIIIb | 0.36 P₁ | −46.5 | DMF | 54 |
| <Glu—Gly—Arg—4-MeO—β-NA | XIV | 0.24 A | −45.7 | 50% HOAc | 36 |
| <Glu— ——OH | XIVa | 0.08 A | — | — | 88 |
| <Glu—Gly—Arg—7-A 4-M—C | XV | 0.25 A | −51.5 | 50% HOAc | 32 |

TABLE IA

Method of Coupling, Purification, etc.; of the foregoing Examples

| Substance No. | |
|---|---|
| I | HF, anisole, G-15 2% HOAc |
| Ia | OpNP, cryst. MeOH |
| Ib | HOBT, DCCI, cryst. MeOH |
| II | HF, anisole, G-15 2% HOAc |
| IIa | HOBT, DCCI, cryst. ether |
| IIb | HOBT, DCCI, cryst. EtOH + H₂O |
| III | HF, anisole, G-15 2% HOAc |
| IIIa | HOBT, DCCI, cryst. EtOAc |
| IIIb | HOBT, DCCI, cryst. EtOAc + petr. ether |
| IV | HF, anisole, G-15 2% HOAc |
| IVa | OpNP, cryst. DMF, MeOH + ether |
| IVb | HOBT, DCCI, cryst. EtOH + H₂O |
| V | HF, anisole, G-15 2% HOAc |
| Va | OpNP, cryst. DMF, MeOH + ether |
| Vb | HOBT, DCCI, cryst. acetone + MeOH |
| VI | HF, anisole, QAE-25 95% MeOH |
| VIa | OpNP, cryst. EtOAc + ether |
| VIb | HOBT, DCCI, cryst. DMF + EtOAc |
| VII | HF, anisole, G-15 2% HOAc |
| VIIa | OpNP, cryst. MeOH + H₂O |
| VIIb | HOBT, DCCI, cryst. acetone + MeOH + H₂O |
| VIII | HF, anisole, G-15 2% HOAc |
| VIIIa | OpNP, cryst. MeOH |
| VIIIb | HOBT, DCCI, cryst. MeOH + H₂O |
| IX | HF, anisole, G-15 2% HOAc |
| IXa | OpNP, cryst. EtOAc + ether |
| IXb | HOBT, DCCI, cryst. MeOH + H₂O |
| X | HBr/HOAc, QAE 25 50% EtOH |
| Xa | OpNP, cryst. MeOH + H₂O |
| Xb | HOBT, DCCI, cryst. MeOH + H₂O |
| XI | HBr/HOAc, QAE-25 50% EtOH |
| XIa | OpNP, cryst. MeOH + H₂O |
| XIb | HOBT, DCCI, cryst. acetone + MeOH |
| XII | HOBT, DCCI, cryst. 50% EtOH |
| XIIa | HF, anisole, G-15 2% HOAc |
| XIII | HF, anisole, G-15 10% HOAc |
| XIIIa | OpNP, cryst. EtOAc + EtOEt |
| XIIIb | HOBT, DCCI, cryst. CHCl₃ |
| XIV | 4-MeO—β-NA + PCl₃ (pyridine) + acid |
| XIVa | according to pNA-derivative + trypsin |
| XV | 7-A 4-M—C + PCl₃ (pyridine) + acid |

TABLE II

| Reference | Relative Reaction Rates Enzyme | | | | |
|---|---|---|---|---|---|
| | Pli | Try | FXa Substrate | UK | TA |
| Substrate (= 100) | S-2251 | S-2160 | S-2222 | I | I |
| I | 10 | 330 | 7 | 100 | 100 |
| II | 100 | 360 | 5 | 65 | 130 |
| V | 140 | 370 | 2 | 65 | 150 |
| VI | 310 | 250 | 15 | 50 | 170 |
| VII | 440 | 240 | 10 | 8 | 40 |
| X | 450 | 40 | 0 | 0 | 10 |
| XI | 230 | 60 | 0 | 0 | 10 |

TABLE II-continued

| Reference | Relative Reaction Rates Enzyme | | | | |
|---|---|---|---|---|---|
| | Pli | Try | FXa Substrate | UK | TA |
| Substrate (= 100) | S-2251 | S-2160 | S-2222 | I | I |
| XII | 15 | 340 | 260 | 15 | 120 |

S-2251 = H—D—Val—Leu—Lys—pNA,
S-2160 = Bz—Phe—Val—Arg—pNA,
S-222 = Bz—Ile—Glu—Gly—Arg—pNA (all Kabi Diagnostica, Stockholm, Sweden).
Pli = Plasmin,
Try = Trypsin,
Fxa = Coagulation factor Xa,
UK = Urokinase,
TA = Plasminogen tissue activator.

Sensibility of the reference substrates to the enzyme in question:

| Enzyme | Substrate | Activity (ΔOD/min) obtained with $4 \cdot 10^{-9}$ mol/l enzyme |
|---|---|---|
| Plasmin | S-2251 | 0.040 |
| Trypsin | S-2160 | 0.150 |
| FXa | S-2222 | 0.200 |
| Urokinase | I | 0.040 |
| Tissue activator | I | 0.040 |

Determination of proteases by means of substrates with a removable and physico-chemically determinable group The substrates produced according to the examples are used in the determination of various enzymes in the following ways.

The principle of determination is based upon the fact that the split product obtained by enzymatic hydrolysis presents a UV spectrum essentially different from that of the substrate. Thus, all p-nitroanilide substrates according to the invention, for instance, have their absorption maxima at 310 nm with a molar extinction coefficient of approximately 12000. At 405 nm, the absorption of these substrates has almost entirely ceased. p-Nitroaniline which is released from the substrates in the enzymatic hydrolysis, has its absorption maximum at 380 nm with a molar extinction coefficient of 13200 which at 405 nm has decreased only to 9620. By measuring spectrophotometrically at 405 nm it is, therefore, easy to follow the amount of p-nitroaniline formed which is proportional to the rate of enzymatic hydrolysis which, in turn, is determined by the active amount of enzyme.

To calculate the amount of fluorescent amine formed, the specimens are irradiated in a fluoroscencephotometer with a light having an excitation wavelength (approximately 350 nm for β-naphthylamine and 4-methoxy-β-naphthylamine, and 380 nm for 7-amino-4-methyl-coumarin), and the amount of split-off product is then established by measuring the emitted light (approximately 420 nm for β-naphthylamine and 4-methoxy-β-naphthylamine, and 440 nm for 7-amino-4-methyl-coumarin).

Table II presents the reaction rate of the synthetic substrates with various enzymes. The reaction rate is related to a reference substrate (reaction rate=100) for each enzyme. Some of the reference substrates are known already and available on the market.

The usefulness of the novel substrates according to the invention, and the fact that they are hydrolysed faster by various enzymes than are the substrates hitherto available, is evident from this Table II.

We claim:

1. A diagnostic method for the determination of proteases in a substance which comprises contacting the substance with a compound of the formula:

$$R_1-\text{p-Glu}-A_1-A_2-NH-R_2,$$

wherein
$R_1$ is H or a protective group;
$A_1$ is Gly, Ala, Val, Leu, Ile, Ser, Thr, Pro, Pip, Phe or Tyr;
$A_2$ is Arg or Lys; wherein —NH—Rz is a chromogenic or fluorogenic group which is capable of being split by enzymatic hydrolysis to form a cleavage product of the formula $H_2N-R_2$, the amount of which can be quantified; and then determining the amount of said cleavage product which is formed.

2. Method according to claim 1 wherein $R_1$ representing a protective group is t-butyloxycarbonyl or benzyloxycarbonyl.

3. Method according to claim 1 wherein $R_2$ is p-nitroanilide, β-nitroanilide, 4-methoxy-β-naphthylamide or 7-amino-4-methyl-conmarin.

* * * * *